United States Patent [19]

Davis et al.

[11] Patent Number: 4,982,604
[45] Date of Patent: Jan. 8, 1991

[54] METHOD AND SYSTEM FOR TESTING THE DYNAMIC INTERACTION OF CORING FLUID WITH EARTH MATERIAL

[75] Inventors: R. Michael Davis, Bedford; Eve S. Sprunt, Farmers Branch; M. Scott Quigley, Plano, all of Tex.

[73] Assignee: Mobil Oil Corporation, Fairfax, Va.

[21] Appl. No.: 439,293

[22] Filed: Nov. 20, 1989

[51] Int. Cl.$^5$ ............................................. E21B 49/00
[52] U.S. Cl. ..................................... 73/153; 324/376; 378/62
[58] Field of Search .................... 73/38, 153, 155; 324/376; 378/62

[56] References Cited

U.S. PATENT DOCUMENTS

| | | | |
|---|---|---|---|
| 2,745,057 | 5/1956 | Dotson | 324/376 |
| 2,963,642 | 12/1960 | Arbogast et al. | 73/153 |
| 3,839,899 | 10/1974 | McMillen | 73/38 |
| 4,174,629 | 11/1979 | Striegler | 73/153 |
| 4,531,404 | 7/1985 | Phelps et al. | 73/38 |
| 4,649,483 | 3/1987 | Dixon, Jr. | 364/422 |
| 4,688,238 | 8/1987 | Sprunt et al. | 378/4 |
| 4,722,095 | 1/1988 | Muegge et al. | 378/4 |
| 4,782,501 | 11/1988 | Dixox, Jr. | 378/4 |
| 4,790,933 | 12/1988 | Quigley et al. | 210/96.1 |
| 4,852,400 | 8/1989 | Wingrave | 73/153 |
| 4,893,504 | 1/1990 | O'Meara, Jr. et al. | 73/153 |

Primary Examiner—John Chapman
Assistant Examiner—Kevin D. O'Shea
Attorney, Agent, or Firm—Alexander J. McKillop; Charles J. Speciale; George W. Hager, Jr.

[57] ABSTRACT

A material sample representative of a subsurface formation is tested for its dynamic interaction with a coring fluid. The material sample is subjected to a pressurized and agitating coring fluid to simulate a coring operation. Thereafter the material sample is x-ray scanned to identify the extent of coring fluid invasion during the dynamic interaction of the material sample and the coring fluid.

16 Claims, 3 Drawing Sheets

METHOD AND SYSTEM FOR TESTING THE DYNAMIC INTERACTION OF CORING FLUID WITH EARTH MATERIAL

BACKGROUND OF THE INVENTION

This invention relates to the determination of certain lithological characteristics of a subsurface formation and more particularly to a method and system for testing a material sample representing the subsurface formation for its dynamic interaction characteristics with a coring fluid which might be utilized during a borehole operation for obtaining a core sample of such subsurface formation.

In the production of minerals, specifically oil and gas, it is common to "engineer" the producing reservoir to improve the economic performance thereof. To do this, certain lithological properties of the reservoir must be determined, the two most important of these properties being the permeability and the porosity of the reservoir rock. Permeability is a measure of the ability of a material to transmit fluids through pore spaces of the mineral and is inversely proportional to the flow resistance offered by the material. Porosity of a material is defined as the ratio of the aggregate volume of its void or pore spaces to its gross bulk volume. In the case of an oil reservoir, porosity is a measure of the volume within the reservoir rock which is available for storing oil and gas. Normally, porosity and permeability, as well as other chemical or physical characteristics of an earth material, are determined from core samples by applying well-defined measurement procedures.

Coring samples are ordinally taken by means of a core drill and the samples obtained are in the form of cylinders or cores. Drilling muds with a water or oil base are commonly used as coring fluids. These drilling muds are normally formulated to provide desired density and rheological properties which make them particularly suitable for use in coring wells. For example, drilling muds may be altered to increase the density by adding solid materials, such as barium sulfate, thereto. During the coring of a subsurface formation, contamination of a core sample by the drilling mud can readily occur. The core material, being porous, will be penetrated by the drilling mud filtrate under the pressure conditions present in the well. Depending on the size of the pore throats in the core material, mud solids (barite, clay minerals and rock cuttings) may also penetrate the core material. The extent of mud solids contamination of core samples must be taken into account when analyzing such core samples to identify certain subsurface formation lithological characteristics, such as porosity and permeability as examples.

In view of the foregoing, it is an object of the present invention to simulate, or model, the dynamic interaction of coring fluid on a material sample representative of a select subsurface formation, both consolidated and unconsolidated, so as to provide a measure of the extent to which a coring fluid will invade a core sample from the select formation during a conventional coring operation. This and other objects of the present invention will become apparent from the following detailed description thereof.

SUMMARY OF THE INVENTION

The present invention is directed to a method and system for testing the dynamic interaction of a material sample representative of a subsurface formation and a coring fluid. The material sample is placed in a holder having an open upper end and a closed lower end with a fluid drain, such holder being comprised of a material permitting transmission of x-rays. The upper surface of the material sample is exposed directly to a coring fluid. A dynamic interaction is effected between the material sample and the coring fluid by pressurizing and agitating the coring fluid while in direct contact with the upper surface of the material sample. Coring fluid filtrate resulting from such a dynamic interaction is removed from the material sample by way of drainage through the fluid drain in the lower end of the holder. The material sample is thereafter scanned with x-rays through the holder. Computed tomographic images produced by the x-ray scanning provide a measure of the extent of the coring fluid invasion of the material sample from the density contrast created in the computed tomographic images by the presence of coring fluid solids in the material sample.

DESCRIPTION OF THE PREFERRED EMBODIMENT

Before describing the method and system of the present invention relating to testing for the dynamic interaction of coring fluid on earth material of subsurface formations, a coring system which may be used for carrying out a subsurface coring operation will first be described in conjunction with FIG. 1.

Figure 1:
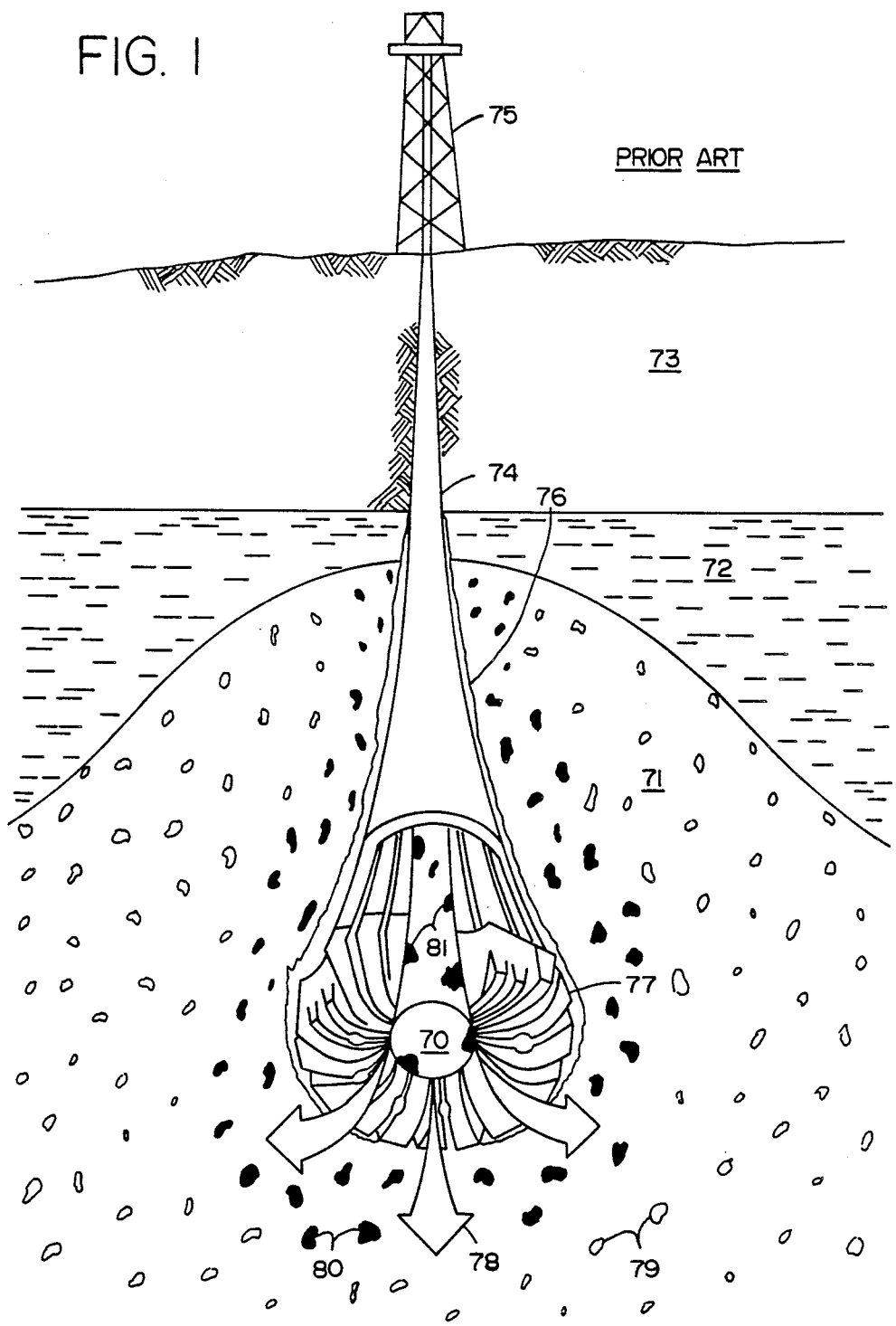
FIG. 1 illustrates in pictorial form a typical prior art subsurface coring operation.

Referring now to FIG. 1, a typical coring system of the prior art is shown in pictorial form obtaining a core sample 70 from a subsurface formation 71 underlying formations 72 and 73. Drill pipe 74 extends from the surface rig 75 through a wellbore 76 to the subsurface formation of interest 71. By drilling into the formation 71 with a coring bit 77, the solid core 70 of uncut formation enters the inner cylinder or core barrel of the coring bit 77. This solid core 70 is later removed from the core barrel at the earth's surface. For more details as to such a typical bottomhole coring operation reference may be had to U.S. patent application Ser. No. 213,810, now U.S. Pat. No. 4,848,487 entitled "Method for Minimizing Mud Solids Invasion of Core Samples Obtained During Subsurface Coring", filed June 30, 1988 to Anderson, Sprunt, Wilson and Wooten, the teachings of which are incorporated herein by reference.

As seen in FIG. 1, coring fluid flows out of the coring bit 77 as shown by the arrows 78. This coring fluid penetrates the formation just in front of the coring bit. In certain formations such as vuggy limestones and highly permeable sandstones, such coring fluid penetration can be a problem. A plurality of vugs 79, or pore spaces, in such formations are shown in FIG. 1. As the drilling fluid penetrates the formation directly ahead of the coring bit, those vugs in the near vicinity of the coring bit are filled with the coring fluid as shown in the plurality of filled-in vugs 80. The coring fluid enters the core sample 70 before and as it is being drawn into the coring bit 77. Consequently the core sample is permeated with the coring fluid before any filter cake can form about the core sample. Mud solids in the coring fluid collect in the vugs 81 shown in the core sample 70 due to dynamic filtration through the core sample. Such mud solids occupy pore space that in the petroleum reservoir is occupied by reservoir fluids and, as a foreign solid present in the sample of the reservoir formation, adversely affect all core analysis measurements of the samples. A common mud solid component in coring fluids is barite which is insoluble in most cleaning solutions. Barite is not easily removed from the occupied pore spaces of the core sample, either chemically or mechanically, by any of the typical cleaning methods mentioned above.

It is therefore a specific aspect of the present invention to provide a method and system for testing for such unwanted invasion of whole mud solids into core samples of subsurface materials during coring operations. In accordance with this aspect of the invention, a material sample that is representative of a consolidated or unconsolidated subsurface formation is selected for testing as to its dynamic interaction characteristic with coring fluid, such testing being carried out by the use of the system shown in FIG. 2.

Figure 2:
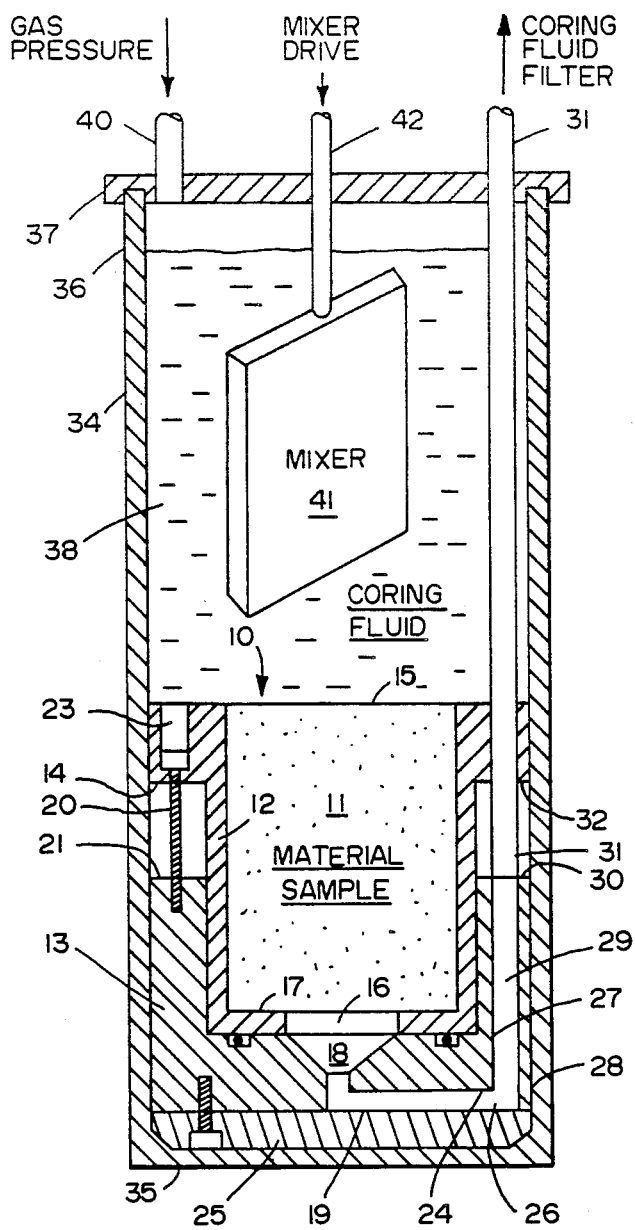
FIG. 2 illustrates apparatus for testing the dynamic interaction of a coring fluid and material sample in accordance with the present invention.

Referring now to FIG. 2, a generally cylindrical hollow material sample holder 10 is open at an upper end 15 and contains a fluid drain centrally located in a lower closed end 17. Holder 10 is filled with a material sample 11 representative of a select consolidated or unconsolidated subsurface earth material to be tested for dynamic interaction with a coring fluid.

Holder 10 is comprised of a generally cylindrical hollow fixture 12 inserted within a generally cylindrical hollow adapter 13. Fixture 12 contains a circumferential flange 14 about open upper end 15 and a fluid drain 16 in closed lower end 17. Adapter 13 contains a truncated fluid passageway 18 centrally located in a closed end 19. Passageway 18 is in fluid communication with drain 16 of fixture 12. Flange 14 of fixture 12 is bored at 23 to receive a fastener 20 which extends through flange 14 and threadably engages the upper end 21 of adapter 13.

Adapter 13 includes a recess 24 along a portion of its lower end 19 which is covered by a bottom plate 25 to form a fluid channel 26 leading radially outwardly from the truncated fluid passagway 18. Adapter 13 further includes a hole 27 bored through a portion of its upper surface which is also connected to fluid channel 26 covered by the bottom plate 25 to form a fluid channel 29 leading upwardly along the length of adapter 13 from the fluid channel 26. The open end of fluid channel 29 at the upper end 30 of adapter 13 is fitted with a tube member 31 which extends through a recess through flange 32.

When affixed together as shown in FIG. 2, the fixture 12 and adapter 13 with its base plate 25 comprise the generally cylindrical material sample holder 10. The outside diameter of holder 10 permits its slidable insertion into a generally cylindrical hollow test cell 34. Test cell 34 is closed at a lower end 35 and is sealed at an upper open end 36 by a cover 37. With the holder 10 inserted into the lower portion of test cell 34, an upper chamber 38 is formed which is filled with a select coring fluid. Since the upper end 15 of fixture 12 of holder 10 is open, the coring fluid will be in direct contact with the upper surface of material sample 11.

To test the dynamic interaction of the coring fluid and the material sample, it is necessary to agitate the coring fluid and at the same time provide suitable pressure conditions within the chamber 38 so that the coring fluid interaction with the material sample will simulate, or model, the dynamic interaction that such a coring fluid and material sample would experience in a subsurface coring operation. Accordingly, the coring fluid is pressurized from a suitable gas pressure supply by means of a passageway 40 through cover 37. Agitation to the coring fluid is supplied by any suitable mixer 41 suspended within the coring fluid and driven by a mechanical drive 42 through cover 37. In the alternative, the coring fluid could be agitated by continuously circulating the coring fluid or even by shaking the test cell 34 as examples.

As the dynamic interaction takes place between the coring fluid and material sample, coring fluid invades material sample. Coring fluid solids remain in the pore spaces of the material sample while coring fluid filtrate passes from the lower end of the material sample through the drain 16, the truncated passageway 18, the channels 26 and 29 and up the tube 31 through a passageway in the cover 37 to a filtrate collection unit (not shown).

Upon termination of the dynamic interaction testing of the coring fluid and material sample, the holder 10 is removed from the test cell 34 and the material sample x-ray scanned to identify the extent of coring fluid invasion of the material sample from a density contrast created in computed tomographic images produced by such x-ray scanning. It is a specific feature of the present invention to subject the material sample to x-rays without disturbing the material sample by its being removed from the holder 10. This is carried out by providing a fixture 12 which comprises a material that allows for the transmission of x-rays, such as aluminum, acrylic or teflon as examples. Fixture 12 is removed from adapter 13 by disengaging fastener 20 and then placed in the computer tomography (CT) scanning system of FIG. 3.

Figure 3:
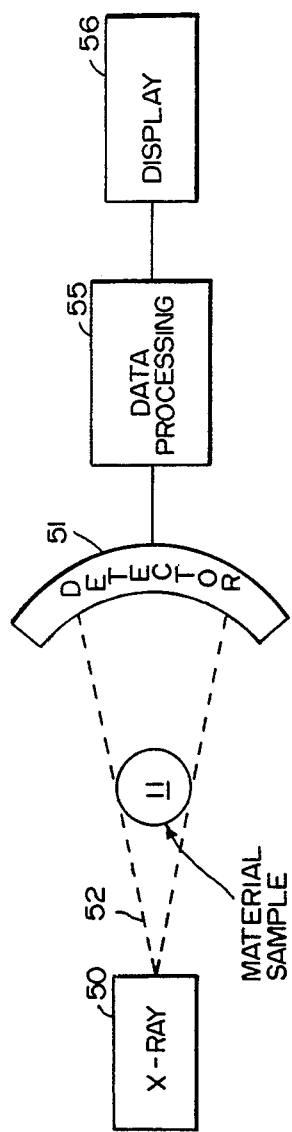
FIG. 3 is a pictorial view of a CT scanning system for use in scanning the material sample with x-rays in accordance with the present invention.

Referring to FIG. 3, X-ray energy provided by the x-ray tube 50 passes through the material sample 11 and fixture 12 (not shown) and falls on the detector array 51. Rotation of fixture 11 within the x-ray fan beam 52 is provided by suitable gantry means (not shown). In an alternative embodiment, the material sample 11 may remain stationary and the gantry may be used to rotate the x-ray tube 50 and detector 51 about the material sample. In medical applications, CT scanning rates are usually in the order of 2 to 9 seconds. However, patient dose limitations are of no concern in the present application, and scan times of the core sample can be up to 30 seconds per scan. The output of the detector 51 is passed through the data processing unit 55 to the display unit 56. After a desired number of translations are completed for a core sample slice, the sample is indexed one slice-width through the x-ray fan beam to place the next adjacent sample slice within the path of the x-ray fan beam. In this manner, a 3-D tomographic presentation is made of the entire sample by compositing the cross-sectional view of each of the scan slices. Such a CT scanning system, while not forming a part of the present invention, is used in accordance with the method of the present invention to quantify the coring fluid solid content in the material sample and thereby identify the extent of coring fluid invasion of the material sample having taken place during the dynamic interaction testing of the coring fluid and the material sample. For more details as to such a CT scanning system, reference may be made to U.S. Pat. Nos. 4,649,483 to Dixon; 4,688,238 to Sprunt et al.; 4,722,095 to Muegge et al. and 4,782,501 to Dixon, the teachings of which are incorporated herein by reference.

Having now described a preferred embodiment of the present invention, it is to be understood that various modifications and changes may be made thereto without departing from the spirit and scope of the invention as set forth in the appended claims.

What is claimed is:

1. A method for testing the dynamic interaction of a material sample representative of a subsurface formation and a coring fluid, comprising the steps of:
   (a) placing said material sample in a holder having an open upper end and a closed lower end with a fluid drain, said holder being comprised of material permitting transmission of x-rays,
   (b) exposing the upper surface of said material sample placed within said holder directly to a coring fluid,
   (c) dynamically interacting said coring fluid and said material sample by simultaneously pressurizing and agitating said coring fluid in direct contact with the upper surface of said material sample,
   (d) removing coring fluid filtrate resulting from the dynamic interaction of said coring fluid and said material sample by way of drainage through the fluid drain in the lower end of said holder,
   (e) scanning said material sample through said holder with x-rays after completing the step of dynamic interacting of said coring fluid and said material sample,
   (f) producing computed tomographic images from said scanning of said material sample, and
   (g) determining the extent of coring fluid invasion of said material sample from a density contrast created in said computed tomographic images by the presence of coring fluid solids within said material sample.

2. The method of claim 1 wherein said step of dynamically interacting said coring fluid and said core sample is carried out for a time period representative of the actual dynamic coring fluid filtration that would occur during coring operations of a subsurface formation containing such a material sample.

3. The method of claim 2 wherein the inside depth of said material sample holder is at least one half of the diameter of a core sample from said subsurface formation such that coring fluid invasion from the surface to the center of such a core sample obtained during coring operations of a subsurface formation containing such a material sample is simulated.

4. A system for testing the dynamic interaction of a coring fluid and a material sample representative of a subsurface formation, comprising:
   (a) a material sample holder,
   (b) an opening in an upper end of said holder through which said holder may be filled with a material sample representative of a subsurface formation and through which said material sample is directly and dynamically interacted with a coring fluid;
   (c) a fluid drain in the lower end of said holder through which coring fluid filtrate passes after dynamic interaction of said coring fluid with said material sample,
   (d) a test cell housing said material sample holder in a lower portion thereof and said coring fluid in a top portion thereof, said coring fluid being in direct contact with said material sample through said opening in the upper end of said holder, and
   (e) a means associated within said upper portion of said test cell for agitating said coring fluid to provide the dynamic interaction between said coring fluid and said material sample.

5. The system of claim 4 further comprising means for pressurizing said test cell to enhance the dynamic interaction of said coring fluid and said material sample.

6. The system of claim 4 wherein at least that portion of said material sample holder that contacts said material sample is comprised of a material that is transparent to x-rays.

7. The system of claim 6 wherein said portion of said holder is comprised of aluminum.

8. The system of claim 6 wherein said portion of said holder is comprised of acrylic.

9. The system of claim 6 wherein said portion of said holder is comprised of teflon.

10. The system of claim 6 further comprising means for x-ray scanning said material sample within the confines of said portion of said holder upon termination of dynamic interaction of said coring fluid and said material sample to identify the depth of coring fluid invasion of said material sample.

11. A system for testing the dynamic interaction of a coring fluid and a material sample representative of a subsurface formation comprising:
   (a) a hollow cylindrical material sample holder, said holder being open at an upper end through which a material sample representative of a subsurface formation may be inserted and having a fluid drain centrally located in a lower end,
   (b) a hollow cylindrical test cell closed at a lower end and open at an upper end, the inside diameter of said test cell permitting the slidable insertion of said material sample holder through the open upper end of said test cell so that said holder rests in the lower portion of said test cell;
   (c) a coring fluid occupying the upper portion of said test cell above said holder such that there is direct contact between said coring fluid and said material sample through the open upper end of said holder,
   (d) a cover for sealing the open end of said test cell,
   (e) means for supplying pressure to said coring fluid,
   (f) means for supplying agitation to said coring fluid, the combination of said pressure and said agitation to said coring fluid creating a dynamic interaction of said coring fluid and said material sample, and
   (g) means in the lower end of said holder for carrying away coring fluid filtrate that drains from said material sample in response to the dynamic interaction of said coring fluid and said material sample.

12. A system of claim 11 wherein said agitation means comprises an agitation device suspended with said coring fluid.

13. The system of claim 12 further comprising:
   (a) a first passageway in said cover through which said gas pressure is applied to said coring fluid,
   (b) a second passageway in said cover through which said agitation means is driven, and
   (c) a third passageway in said cover through which said coring fluid filtrate is carried away.

14. The system of claim 11 wherein at least that portion of said material sample holder that contacts said material sample comprises a material that permits the transmission of x-rays for examining the depth of coring fluid penetration of said material sample during its dynamic interaction with said coring fluid.

15. The system of claim 11 wherein said material sample holder comprises:
(a) a generally cylindrical fixture for containing said material sample, said fixture having an open upper end for receiving said material sample and a closed lower end, said fluid drain being centrally positioned in the closed lower end of said fixture,
(b) a generally hollow cylindrical adapter having an open end for slidably receiving the lower end of said fixture and a closed lower end,
(c) a first fluid passageway extending through said adapter in fluid communication with the fluid drain in said fixture, and
(d) means connected to said first fluid passageway for carrying said coring fluid filtrate away from said adapter.

16. The system of claim 15 further comprising:
(a) a circumferential flange around the upper end of said fixture,
(b) a second fluid passageway extending through said flange,
(c) a third fluid passageway extending through said cover, and
(d) means for connecting said first fluid passageway in said adapter, said second fluid passageway in the flange of said fixture, and said third fluid passageway in said cover to provide an exit from said test cell for coring fluid filtrate drainage from said material sample.

* * * * *